US010475356B2

(12) United States Patent
Becker et al.

(10) Patent No.: US 10,475,356 B2
(45) Date of Patent: Nov. 12, 2019

(54) SHEETED MEDICAL ARTICLES WITH ADHERED WRISTBAND

(71) Applicant: CCL Label, Inc., Framingham, MA (US)

(72) Inventors: William Becker, Rockport, NY (US); Zbigniew Krauze, Lancaster, NY (US)

(73) Assignee: CCL LABEL, INC., Framingham, MA (US)

( * ) Notice: Subject to any disclaimer, the term of this patent is extended or adjusted under 35 U.S.C. 154(b) by 0 days.

(21) Appl. No.: 15/568,922

(22) PCT Filed: Apr. 25, 2016

(86) PCT No.: PCT/US2016/029146
§ 371 (c)(1),
(2) Date: Oct. 24, 2017

(87) PCT Pub. No.: WO2016/172676
PCT Pub. Date: Oct. 27, 2016

(65) Prior Publication Data
US 2018/0114467 A1    Apr. 26, 2018

Related U.S. Application Data

(60) Provisional application No. 62/152,419, filed on Apr. 24, 2015.

(51) Int. Cl.
*G09F 3/00* (2006.01)
*A61B 90/94* (2016.01)
(Continued)

(52) U.S. Cl.
CPC .............. *G09F 3/005* (2013.01); *A61B 90/94* (2016.02); *B32B 5/022* (2013.01); *B32B 7/12* (2013.01);
(Continued)

(58) Field of Classification Search
CPC .... G09F 3/005; G09F 3/10; G09F 2003/0241; G09F 2003/0239; B32B 27/36;
(Continued)

(56) References Cited

U.S. PATENT DOCUMENTS 10,311,758 B2 *    6/2019    Becker ................. G09F 3/0289
2004/0113421 A1    6/2004    Penuela et al.
(Continued)

OTHER PUBLICATIONS

Patent Cooperation Treaty (PCT), International Search Report and Written Opinion for Application PCT/US2016/029146 filed Apr. 25, 2016, dated May 8, 2016, International Searching Authority, EP.

*Primary Examiner* — Patricia L. Nordmeyer
(74) *Attorney, Agent, or Firm* — McDonald Hopkins LLC

(57) ABSTRACT

Various sheeted articles are described. The articles include one or more banding products such as wristbands or ankle bands. The banding products are securely retained within the sheet articles prior to use by one or more regions of adhesive. Upon removal of the banding products from the sheet, one end of the band (an attachment end) comprises an adhesive to allow attachment to the other end, and the second end including the strap portion is generally free of any adhesive or liner material and the under surface of the second end is substantially formed by the material of the face layer. The articles can also include a collection of removable adhesive backed labels.

25 Claims, 7 Drawing Sheets

(51) Int. Cl.
*C09J 7/29* (2018.01)
*B32B 5/02* (2006.01)
*B32B 7/12* (2006.01)
*B32B 27/36* (2006.01)
*G09F 3/10* (2006.01)
*G09F 3/02* (2006.01)

(52) U.S. Cl.
CPC ............... *B32B 27/36* (2013.01); *C09J 7/29* (2018.01); *G09F 3/10* (2013.01); *B32B 2307/748* (2013.01); *C09J 2201/162* (2013.01); *C09J 2201/40* (2013.01); *C09J 2201/606* (2013.01); *C09J 2203/334* (2013.01); *C09J 2205/10* (2013.01); *C09J 2400/263* (2013.01); *C09J 2467/006* (2013.01); *G09F 2003/0239* (2013.01); *G09F 2003/0241* (2013.01)

(58) Field of Classification Search
CPC ..... B32B 7/12; B32B 5/022; B32B 2307/748; C09J 7/29; C09J 2467/006; C09J 2400/263; C09J 2205/10; C09J 2203/334; C09J 2201/606; C09J 2201/40; C09J 2201/162; A61B 90/94
See application file for complete search history.

(56) References Cited

U.S. PATENT DOCUMENTS

2011/0041370 A1  2/2011  Saint et al.
2012/0258271 A1  10/2012  Maughan

* cited by examiner

SHEETED MEDICAL ARTICLES WITH ADHERED WRISTBAND

CROSS-REFERENCE TO RELATED APPLICATION

The present application is a 35 U.S.C. 371 national stage filing of PCT Application No. PCT/US2016/029146 filed on Apr. 25, 2016, which claims priority to U.S. Provisional Application No. 62/152,419 entitled "Sheeted Medical Articles with Adhered Wristbands," filed on Apr. 24, 2015, the disclosures of each of which are incorporated by reference herein in their entirety.

FIELD OF THE INVENTION

The present subject matter relates to sheeted and web based products such as used in certain medical articles and applications and to materials suitable for such products. The sheeted articles are particularly well suited for use in association with patient identification products, including wristbands and ankle bands, and those which are conveniently provided in a printable sheet form.

BACKGROUND

To help prevent medical errors due to patient misidentification, many hospitals and other heath care providers use patient identification bands, which are secured around a patient's wrist or ankle. Printed on or attached to such identification bands is information such as a patient's name, date of birth, identification number, and sometimes even the patient's picture and an assigned barcode. In addition, identification bands or other medical articles can receive other indicia or markings. Such information or markings can be applied upon the band or article by use of a conventional printer such as a laser printer, an inkjet printer, or a thermal printer for example. Prior to printing upon the band or article, it is preferred that the article be residing in a sheet form so that the sheet(s) containing the band or article can be fed directly into the printer. This practice requires that the band, article, and/or sheet containing such, be relatively thin and yet be sufficiently stable and rigid to undergo feeding and passage into the printer. Thus, the sheet and its component layers and materials must withstand the mechanical and thermal stresses of printing or other like operation.

Sheeted medical articles are known in the art, including those which carry or incorporate one or more band products such as wristbands or ankle bands. For patients with delicate or sensitive skin, it would be desirable to provide a skin contacting material in an identification band that is soft and does not irritate the skin. Although such materials are somewhat known in the art, they are typically expensive and/or are difficult to incorporate in a sheet or web form. Also, problems may arise with certain sheeted articles if the relatively long band products are not firmly retained in the sheet during printing or other operations prior to removal and affixment to a patient. For example, the band products may lift up or become detached along one or more edges from their associated sheet and thereby become lodged in a printer. In addition, the bands may undergo wrinkling or other unwanted changes.

Accordingly, a need exists for a sheeted article providing one or more band products which are securely retained in the sheet, yet which can be readily removed when desired. Moreover, it would be particularly desirable to provide such a sheeted article that can withstand the mechanical and thermal stresses of printing, exhibits desirable skin-contacting qualities such as softness, and is relatively inexpensive.

SUMMARY

The difficulties and drawbacks associated with previously known products and practices are addressed in the present products and methods for sheeted or web based medical articles.

In one aspect, the present subject matter provides a sheeted article providing at least one identification band comprising a face layer having an upper surface and a lower surface and defining at least one identification band, the at least one identification band having a first region proximate a first end, and a second region defined by a second end and a strap extending between the first and second end; a liner layer; a release material disposed on the liner layer in an area corresponding to the first region of the band; a first adhesive overlying the release material; a second adhesive disposed on the liner extending along at least a majority in an area corresponding to the second region of the band; and a deadener disposed on the second adhesive; wherein upon removal of the identification band from the sheeted article, the first region of the identification band comprises the region of pressure sensitive.

In one embodiment, upon removal of the identification band from the sheet, the second region is free of deadener.

In one embodiment, the subject matter provides a sheeted article of any previous embodiment, wherein the first adhesive is a pressure sensitive adhesive.

In one embodiment, the subject matter provides a sheeted article of any previous embodiment, wherein the second adhesive is a permanent adhesive.

In one embodiment, the subject matter provides a sheeted article of any previous embodiment, wherein the release material first adhesive is substantially coextensive with the release material.

In one embodiment, the subject matter provides a sheeted article of any previous embodiment, wherein the deadener is substantially coextensive with the second adhesive.

In one embodiment, the subject matter provides a sheeted article of any previous embodiment, wherein the face layer is formed from paper, a woven material, a non-woven material, a spun material, a polymer film, or a combination of two or more thereof.

In one embodiment, the subject matter provides a sheeted article of any previous embodiment, wherein the face layer comprises a material chosen from a polyethylene, a polypropylene, a polyethylene terephthalate, a polyvinyl chloride, or a combination of two or more thereof.

In one embodiment, the subject matter provides a sheeted article of any previous embodiment, wherein the face layer comprises a non-woven polyester material laminated to a polyester film. In on embodiment, the non-woven polyester film forms the lower surface of the face layer. In still another embodiment, the non-woven polyester material has a thickness of from about 1 mil to about 4 mils, and the polyester film has a thickness of from about 0.5 mils to about 4 mils.

In one embodiment, the subject matter provides a sheeted article of any previous embodiment, wherein the first adhesive comprises a first permanent adhesive and the second adhesive comprises a second permanent adhesive. In one embodiment, the first permanent adhesive is different than the second permanent adhesive.

In one embodiment, the subject matter provides a sheeted article of any previous embodiment, wherein (a) the face layer comprises (i) a label region with at least one label defined therein, and (ii) a third adhesive on the lower surface of the face layer along the label; and (b) the liner layer comprises a release material in an area corresponding to the label region.

In another aspect, the present invention provides a method of forming a sheeted article having a removable identification band, the method comprising: providing a face layer having an upper surface and a lower surface; die cutting a band in the face layer, the band having a first region proximate a first end, and a second region defined by a second end and a strap extending between the first and second end; providing a liner layer comprising an upper surface and a lower surface; applying a release coating on the upper surface of the linear in a region corresponding to the first region of the band; applying a first adhesive over the release agent; applying a second adhesive on the upper surface of the liner in a region corresponding to the second region of the band; applying a deadener over the second adhesive; and mating the face layer with the liner layer.

In one embodiment, the subject matter provides the method of any previous embodiment, wherein the first adhesive is a pressure sensitive adhesive.

In one embodiment, the subject matter provides the method of any previous embodiment, wherein the second adhesive is a permanent adhesive.

In one embodiment, the subject matter provides the method of any previous embodiment, wherein mating is performed by aligning the face layer with the liner layer and contacting the lower surface of the face layer with the upper surface of the liner layer.

In one embodiment, the subject matter provides the method of any previous embodiment further comprising die cutting at least one label in a label region of the face layer.

In one embodiment, the subject matter provides the method of any previous embodiment further comprising applying a pressure sensitive adhesive along the lower surface of the label region of the face layer.

In one embodiment, the subject matter provides the method of any previous embodiment further comprising applying a release agent to the upper surface of the liner layer in a region that will register with the label region of the face layer.

In one embodiment, the subject matter provides the method of any previous embodiment, wherein the face layer is formed from paper, a woven material, a non-woven material, a spun material, a polymer film, or a combination of two or more thereof.

In one embodiment, the subject matter provides the method of any previous embodiment, wherein the face layer comprises a material chosen from a polyethylene, a polypropylene, a polyethylene terephthalate, a polyvinyl chloride, or a combination of two or more thereof.

In still another aspect, the present subject matter provides a sheeted article providing at least one identification band comprising: a face layer having an upper surface and a lower surface and defining at least one identification band, the at least one identification band having a first region proximate a first end, and a second region defined by a second end and a strap extending between the first and second end; a dry peel release coating disposed on the lower surface of the face layer within the second region; a liner layer; a release material disposed on a first region of the liner layer proximate and in contact with the region of pressure sensitive adhesive; and a region of pressure sensitive adhesive overlying the release material; a permanent adhesive disposed on a second region of the liner extending along at least a majority of the strap and the second end of the band defined by the face layer.

In one aspect, the present subject matter provides a sheet assembly comprising at least one sheet that includes fibrous material comprising cellulose fibers and nylon fibers intermingled with the cellulose fibers to thereby form a fibrous matrix. The fibrous material also comprises synthetic latex dispersed throughout the fibrous matrix.

In another aspect, the present subject matter provides a sheet assembly comprising a face sheet, and a backing sheet at least partially formed from a fibrous material. The fibrous material comprises cellulose fibers, and nylon fibers intermingled with the cellulose fibers to thereby form a fibrous matrix. The fibrous material also comprises synthetic latex dispersed throughout the fibrous matrix.

In another aspect, the present subject matter provides a method of forming an article having a skin-contacting face with improved softness. The method comprises incorporating a fibrous material in the article such that the fibrous material constitutes a skin-contacting face of the article. The fibrous material includes (i) cellulose fibers, (ii) nylon fibers intermingled with the cellulose fibers to thereby form a fibrous matrix, and (iii) synthetic latex dispersed throughout the fibrous matrix.

In one aspect, the present subject matter provides a medical article in sheet form comprising a face layer defining a top surface and an oppositely directed back surface. The face layer includes a first region including a paper material and a second region including a fibrous material including at least two populations of fibers bonded to one another. The first region and the second region are generally coplanar with one another. The face layer also defines at least one band in the second region of the face layer. The band has a first end, a second end, and a strap extending between the ends. The article also comprises a liner layer defining a top surface and an oppositely directed back surface. The article additionally comprises a first adhesive layer disposed between the face layer and the liner layer, the first adhesive layer extending proximate the first end of the band. The article also comprises a second adhesive layer disposed between the face layer and the liner layer. The second adhesive is different than the first adhesive. The second adhesive layer extends along the strap of the band. The article also comprises at least one release layer disposed alongside the first adhesive layer and the second adhesive layer.

In another aspect, the present subject matter provides a sheeted article providing at least one identification band. The sheeted article comprises a face layer including a fibrous material. The face layer defines at least one identification band. The band has a first end, a second end, and a strap extending between the first end and the second end. The article also comprises a liner layer, a region of a pressure sensitive adhesive extending along at least a majority of the first end of the band defined in the face layer, a region of a permanent adhesive extending along at least a majority of the strap of the band defined in the face layer, and at least one region of a release material in contact with at least one of the region of pressure sensitive adhesive and the region of permanent adhesive.

In still another aspect, the present subject matter provides an identification band. The band has a first end, a second end, and a strap portion extending between the first end and the second end. The band comprises a face layer that defines a top surface and a back surface. The band also comprises a liner layer that defines a top surface and a back surface. The liner layer is positioned along the face layer such that the top surface of the liner layer is directed toward the back surface of the face layer. The band also comprises a region of a first adhesive extending along the strap portion of the band between the face layer and the liner layer. The band also comprises a region of release agent extending along the first end of the band between the face layer and the liner layer. The band also comprises a region of a second adhesive extending along the first end of the band between the face layer and the liner layer and in contact with the region of the release agent. The band additionally comprises a region of a deadener extending along the region of the first adhesive and in contact with the first adhesive. Upon separation of the liner layer from the face layer, the first adhesive and the deadener remain associated with the liner layer.

In still another aspect, the present subject matter provides a method for releasably retaining a removable band in a sheet article including a face layer and a liner layer. The band is separable from the face layer by one or more diecuts defining the band perimeter. The method comprises providing an adhesive along the liner layer extending along at least a portion of the band length. The method also comprises providing a release agent and a deadener between the adhesive and an underside of the face layer. Upon removal of the band from the sheet article and separation from the face layer, the deadener is separated from the release agent and remains adhered to the adhesive on the liner layer, and the release agent accompanies the band.

In yet another aspect, the present subject matter provides a method of forming a sheet article including a removable band. The method comprises providing a face layer defining an underside. The method also comprises die cutting a band in the face layer. The band has a first end, a second end, and a strap extending between the first end and the second end. The method also comprises applying a pressure sensitive adhesive to the underside of the face layer along the first end of the band. The method also comprises applying a release agent to the underside of the face layer along the strap and the second end of the band. The method additionally comprises applying a deadener on the release agent. The method also comprises providing a liner layer defining a top face. The method also comprises applying a permanent adhesive on the top face of the liner layer at a location that will register with the applied release agent. The method also comprises applying a release agent on the top face of the liner layer that will register with the applied pressure sensitive adhesive on the underside of the face layer at the first end of the band. And, the method comprises mating the face layer and the liner layer together to thereby form the sheet article.

In an alternate embodiment, provided is a sheet assembly including a liner layer and a face layer. In this embodiment, a portion of release agent may be disposed on the liner layer at a first region. A correspondingly shaped and sized portion of an adhesive may be disposed on the release agent along the first region. The first region may be comparable to an area aligned with a first end of the band and a second region may be an area aligned to a strap of the band along the face layer. Adhesive may also be disposed on the liner layer and particularly, along the second region. At least one layer of a deadener may be disposed on the liner layer and may be correspondingly shaped and sized relative to the shape and size of the strap of the band. The deadener may be disposed along at least a portion of the second portion. This embodiment allows the band to be removed from the face layer and the liner layer and to transfer the adhesive from the release agent along the first region to the underside of the face layer.

This allows the band to be removed from the sheet without having release agent or deadener remaining on the band. However, it will be appreciated that the present subject matter includes bands having structures or utilizing different materials and/or layers at different regions.

In a further aspect, the present subject matter provides a method for releasably retaining a removable band in a sheet article including a face layer and a liner layer. The band is separable from the face layer by one or more die-cuts defining the band perimeter. The method comprises providing a release agent, such as silicone, for example, along a first region of the liner layer, the first region extending along at least a portion of the band length of the removable band. The method also comprises providing an adhesive over at least a portion of the release agent as well as other portions of the liner layer. Further, a deadener may be applied to a second region of the liner layer, the second region may be separate from the first region. The deadener may be applied to a portion of the liner layer that is aligned with the removable band. The face layer may then be joined with the liner layer into a sheet article. Upon removal of the band from the sheet article and separation from the face layer, the deadener is separated from the release agent and remains adhered to the adhesive on the liner layer, and the adhesive over at least a portion of the release agent, is transferred to the band.

In yet another aspect, the present subject matter provides a method of forming a sheet article including a removable band. The method comprises providing a face layer defining an underside. The method also comprises providing a liner layer defining a top face. The method also comprises applying a release agent to a first region of the top face of the liner layer. The first region may be aligned along an end portion of a strap of the band on the face layer. The method also comprises applying an adhesive layer to the top face of the liner layer over the first region and a second region. The second region is separate from the first region. The method additionally comprises applying a deadener to at least a portion of the second region of the liner layer having adhesive separate from the release agent. And, the method comprises mating the face layer and the liner layer together to thereby form the sheet article. The method also comprises die cutting the band in the face layer forming the band with a first end, a second end, and a strap extending between the first end and the second end such that as the band may be removed from the face layer and liner layer, adhesive applied on the release layer may transfer to the band.

As will be realized, the subject matter described herein is capable of other and different embodiments and its several details are capable of modifications in various respects, all without departing from the claimed subject matter. Accordingly, the description is to be regarded as illustrative and not restrictive.

DETAILED DESCRIPTION

Figure 1:
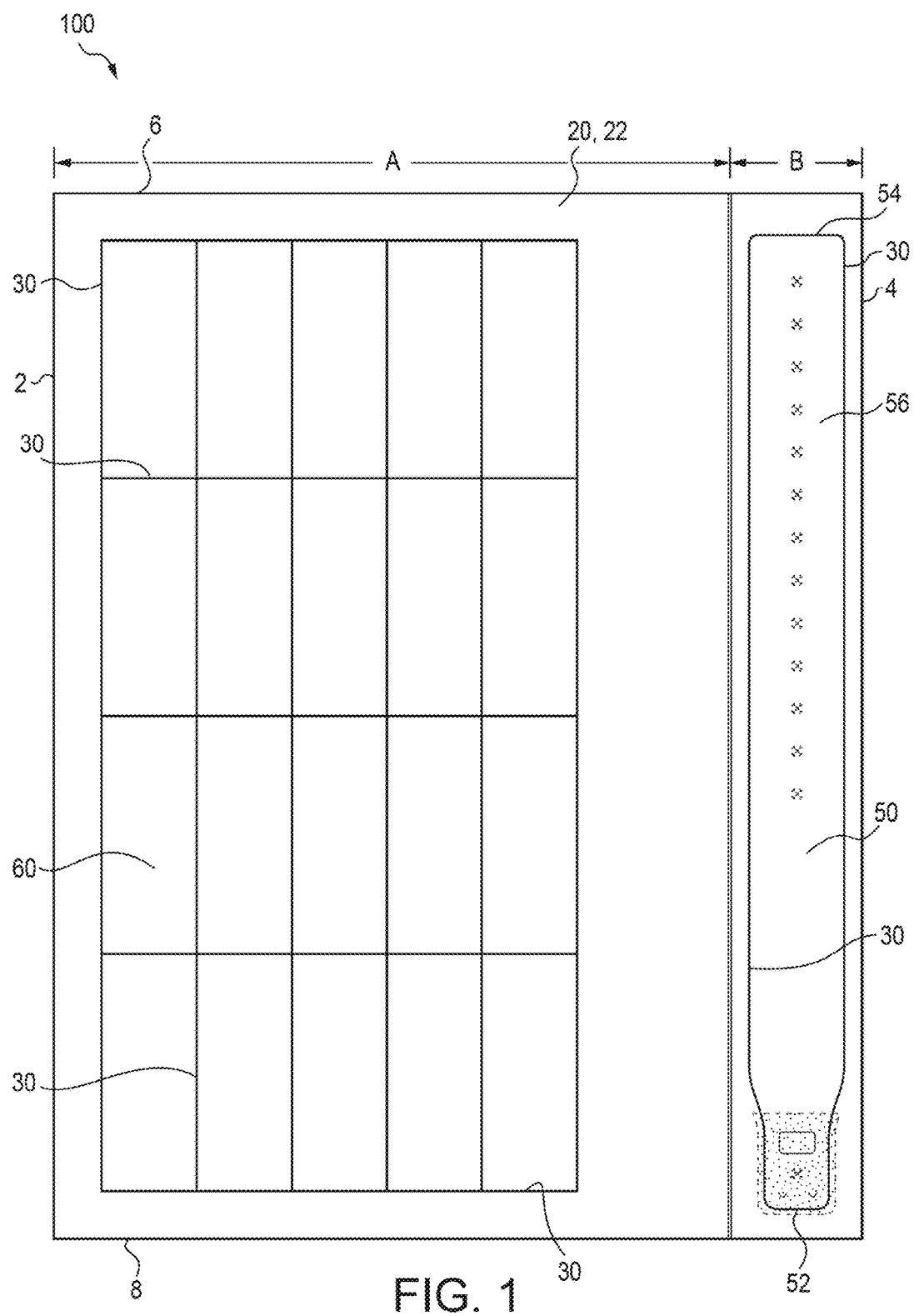
FIG. 1 is a schematic planar view of a sheeted article carrying a removable band in accordance with the present subject matter.

The present subject matter is directed to a sheeted article comprising an identification band. In various embodiments, the sheeted articles include band products such as wristbands and ankle bands, which can be used as, but not limited to, patient identification products and relatively thin laminates used in medical applications. The bands include one or more regions of adhesive along their rear face which ensures that the bands remain securely retained within the sheet until removal. The sheeted articles are provided identification bands such that, in some embodiments, when the band is removed from sheet at least a portion of the band (e.g., the strap region) is free of a liner material and/or free of an adhesive. That is, the sheets may be configured such that at least a portion of a band formed in the sheet substantially comprises just the face layer upon removal from the sheet. In many embodiments of the present subject matter, the sheeted article comprises a soft material to provide a surface that when contacting the skin is not too rough and avoids irritating the skin. In embodiments, a fibrous material can be incorporated into one or more layers of a sheeted article. The fibrous material can be in sheets or webs used to form a variety of medical articles. The fibrous material can be incorporated into a layer such as a face layer, a backing layer, a substrate layer, and/or a skin contacting layer.

Sheeted Article

The sheeted article can comprise any suitable number of layers as desired. Generally, the sheeted articles comprise a top or face layer and a bottom or liner layer and so, utilize a bilayer configuration. The liner/bottom layer can also be referred to herein as a backing layer. In many embodiments, each layer or component includes particular features or combinations of features as described herein. The sheet articles of the present subject matter are not limited to a bilayer configuration. Instead, the present subject matter also comprises sheeted articles that include additional components and/or layers, many of which are described herein. Such layers can include, but are not limited to, a substrate, a skin contacting layer, etc. As previously described, the fibrous material can be used in or as various layers of the sheeted article. In one embodiment, a face layer includes the fibrous material. In another embodiment, a backing layer includes the fibrous material.

The sheeted articles can include additional components or items in association with identification bands. In many of the embodiments described herein, the articles also comprise one or more labels. The labels can receive indicia such as from printing and are readily removable from the sheet. After removal, the labels typically include a layer of a pressure sensitive adhesive along their exposed rear face. Another example of component(s) which may be formed or otherwise included in the sheeted articles is an optional card. Card(s) can be included and may receive indicia or other elements as desired.

Face Layer

The face layer may be formed from any suitable material as desired for a particular purpose or intended application. The face layer may be formed, for example, from paper, a polymeric film, a woven material, a non-woven material, a spun material, etc., or combinations of two or more thereof. In many embodiments of the present subject matter, the face layer is substantially rectangular and can be formed at least partially from a woven material, such as polyester, that has been impregnated with a compatible filler, such as polyester or nylon. The filler is applied sufficiently to define a relatively smooth continuous surface that will accept and retain printed indicia. The filler material impregnated into the woven fabric may be a polyester, styrene, acrylic or other compatible organic-based material. Also, the face sheet can be formed at least partially from a spun material and/or a non-woven material, which can be, for example, polyolefins, polyesters, polyvinyl materials, etc. Examples of polymeric films include polyolefin films, polyester films, polyvinyl films, etc. In embodiments, the face sheet may be formed from a material chosen from polyethylene, polypropylene, polyethylene terephthalate, polyvinyl chloride, or mixtures of two or more thereof. Other materials include vinyl (PVC), polystyrene, latex impregnated paper, polyolefin, and biaxially oriented polypropylene (BOPP). Spun materials are non-woven materials that typically are made from polymeric fibers. The fibers are oriented in a seemingly random orientation to resemble cloth or fabric. The fibers can be bonded together via chemical, mechanical, heat, and/or solvent treatment(s). Woven materials typically are made from fibers that are oriented generally parallel to one another and can be bonded together via chemical, mechanical, heat, and/or solvent treatment(s).

It will be appreciated that the face layer may be formed from different materials in a layered arrangement. For example, the face layer may be formed from a plurality of materials laminated together. The combination of materials employed in a layered face sheet may be selected as desired for a particular purpose or intended application. In one embodiment, the face sheet comprises a combination of a polymeric film and a non-woven material. The polymeric film may be any polymeric film as desired including, for example, a polyolefin, a polyester, a polyvinyl, etc. The non-woven material may also be chosen as desired and can be chosen from, for example, non-woven polyolefin, non-woven polyester, non-woven polyvinyl, etc. In one embodiment, the face sheet comprises a polyester film laminated to a non-woven polyester material. In application in the present invention, the multi-layered face sheet comprising the non-woven material laminated to the polymeric film may be employed in the sheeted article to form the wrist band portion, and the sheet can be arranged such that the non-woven material (e.g., the non-woven polyester) will be the skin-contacting portion of the wristband. As is discussed herein, the polymeric film may be configured (e.g., by application of a coating) to receive printing.

In certain embodiments, the face layer is formed from multiple materials segregated by area or surface region. For example, in certain embodiments, paper or a paper-based material is used in one region of the face layer and a polymeric material such as a woven, spun, or non-woven material can be used in another region of the face layer. A particular embodiment includes a paper material in a region of the face layer at which a plurality of removable labels are provided, and a fibrous material as described herein in a region of the face layer at which one or more bands are provided. In certain embodiments, the multiple regions of different materials, e.g. paper and fibrous materials, are arranged such that they are coplanar with one another. That is, the different materials or regions of different materials are arranged such that they extend generally within a single, common plane. However, it will be appreciated that the present subject matter includes other arrangements and configurations.

It will be appreciated that the face layer may also be formed by multiple layers of materials. For example the face layer may be formed by two, three, four, or more layers of selected materials. In embodiments, the same or similar types of materials may be used to form the individual layers. In other embodiments, the different layers may be formed from different materials. In one embodiment, the face layer may be a multi-layer face layer comprising a non-woven material laminated to a polymeric film material. In one embodiment, the face layer is a multi-layer face layer comprising a non-woven polyester laminated to a polyester film. In one embodiment, the non-woven polyester forms the upper surface of the face layer.

In one embodiment of the present subject matter, a fibrous material is provided that can be incorporated into one or more layers of the sheeted article. The fibrous material generally includes at least one type or population of fibers formed from cellulose, nylon, polypropylene, polyolefin, and similar materials; and at least one emulsion agent such as a natural or synthetic latex material, or an emulsion agent of another polymer with a low glass transition temperature. An example of the fibrous material is a fibrous material that comprises cellulose fibers, synthetic latex and nylon fibers. More specifically, the material comprises cellulose or paper-based fibers and nylon fibers intermingled with one another, and dispersed in a synthetic latex. The components can be combined or assembled in different configurations or combinations. A useful combination is to combine the cellulose fibers with the synthetic latex. This may result in a coating of the latex on all or a portion of the cellulose fibers. In certain versions, the cellulose fibers are coated, impregnated or saturated with the latex. However, the material also includes combining the nylon fibers with the synthetic latex which may result in the nylon fibers being coated, impregnated or saturated with the latex. Moreover, the material also includes combining the cellulose fibers and the nylon fibers concurrently or substantially so, with the synthetic latex.

Generally, the populations of fibers, e.g. the cellulose fibers and the nylon fibers, as described herein, are bonded to one another at all or a portion of their intersecting locations. The term "intersecting locations" as referred to herein refers to locations at which neighboring or adjacent fibers cross one another, contact one another, or substantially cross or contact one another. The bonding can be the result of heat bonding, or result from the latex material at the intersecting location(s) of interest. In certain versions of the present subject matter, at least a portion of the synthetic latex is disposed at intersecting locations of the cellulose and nylon fibers and serves to bond those fibers together. Other techniques for bonding can be used such as solvent bonding, mechanical bonding, ultrasonic bonding, needle punching, hydroentanglement, and stitchbonding. Conventional fiber processing operations can also be used to combine and/or to intermingle the various fibers with one another.

Nearly any type of cellulose fiber can be utilized. Similarly, nearly any type of synthetic latex material can be used. And, depending upon the intended application, a wide array of nylons can be used. The latex material is a synthetic latex material thus designating that the material is preferably not derived from natural rubber sources. A useful guide for the proportion or amount of nylon fibers is based upon the tear strength requirements of the final product. Typically, increasing the proportion of nylon fibers in the material will increase the tear strength of the material. Generally, a majority proportion of cellulose fibers and latex are used, in combination with a minority proportion of nylon fibers. In certain embodiments, the proportion of nylon fibers in the material is about 10% by weight. However, it will be appreciated that the present subject matter includes the use of proportions of these components different than described herein.

The fibrous material can also include a wide array of other fibers, components and agents such as, but not limited to, fibers formed from a wide array of polymeric materials, particulates, antimicrobial agents, UV blockers or similar agents, colorants, pigments, stabilizing agents, or other ancillary components. The material or rather the fibers of the material could receive one or more coatings or have additional materials dispersed within the fibrous matrix. The coatings or additional materials could include for example antimicrobial agents, release agents such as silicone release agents, laser imprintable coatings, or primer coatings. Combinations of any of these are also contemplated.

The thickness of the fibrous material generally depends upon the requirements of the intended application. Typical thicknesses of the material are within a range of from about 3 mils to about 7 mils, and particularly about 6 mils.

A preferred material comprising the previously described cellulose fibers, nylon fibers, and synthetic latex dispersed within the fibrous matrix exhibits the following properties as shown in Table 1.

TABLE 1

Preferred Properties of Fibrous Material

| | | English Units | Metric Units |
|---|---|---|---|
| Caliper (Thickness) | | 5.6 Mils | 142 µ |
| Tensile Strength | MD | 27.0 lbs/inch of width | 47.3 N/cm of width |
| | CD | 22.0 lbs/inch of width | 38.5 N/cm of width |
| Elongation | MD | 6.0 % | 6.0 % |
| | CD | 12.0 % | 12.0 % |
| Elmendorf Tear Resistance | MD | 170 grams | 170 grams |
| | CD | 180 grams | 180 grams |
| Opacity | | 70 % | 70 % |
| Brightness | | 90 % | 90 % |
| Basis Weight | | 60.0 lbs/3000 ft² | 97.6 gsm |

Elemendorf Tear Resistance is determined in accordance with TAPPI T414. Tear Strength is determined in accordance with ASTM D624. Elongation is determined in accordance with TAPPI T404. Opacity is determined according to TAPPI T425. And, brightness is determined by TAPPI T525.

Generally, the fibrous material comprising cellulose fibers, nylon fibers, and synthetic latex can exhibit a range of properties and is not limited to the particular properties set forth in the table above. For example, the fibrous material may exhibit a tensile strength in the machine direction (MD) of from about 20 to about 35 lbs/inch of width, and in the cross direction (CD) of from about 15 to about 30 lbs/inch of width. The fibrous material may exhibit an elongation in the machine direction of from about 2% to about 15%, and in the cross direction of from about 6% to about 25%. The fibrous material may exhibit an Elmendorf Tear value in the machine direction of from about 100 to about 300 grams, and in the cross direction of from about 100 to about 320 grams. The fibrous material may exhibit an opacity of from about 50% to about 90%. The fibrous material may exhibit a brightness of from about 70% to about 95%. And, the fibrous material may exhibit a basis weight of from about 30 to about 120 lbs/3000 ft$^2$. It will be understood that the present subject matter includes similar fibrous materials exhibiting different properties and/or combinations of properties than these.

The fibrous material(s) described herein exhibit remarkably soft characteristics. Layers of the fibrous material are soft to the skin and are non-irritating.

The face layer in certain embodiments has a thickness of about 5 mils, and can range in thickness from about 1.0 mil to about 6.0 mils. When the face layer is a multi-layer construction, the thickness of the respective layers may be selected as desired to provide a face layer having an overall, desired thickness (e.g., from about 1.0 to about 6.0 mils). In one embodiment, the face layer comprises (i) a an upper layer having a thickness of from about 1.0 mils to about 4 mils; from about 1.5 mils to about 3.5 mils; even about 2.0 mils to about 2.5 mils; and (ii) a bottom layer having a thickness of from about 0.5 mils to about 4 mils; from about 1.0 mils to about 3 mils; even about 1.5 mils to about 2.5 mils. As noted, the face layer typically receives printed indicia. The printed indicia can include, for example, high-resolution images and/or a barcode, e.g., a 2-D barcode or a 3-D barcode.

Generally, one or more identification bands or their perimeter are defined on the face layer by a corresponding plurality of arrays of die cuts. The die cut arrays can be die cut, laser cut or otherwise formed to extend through or substantially through the face layer at a plurality of spaced apart locations thereon. The specific dimensions of the die cut arrays can vary depending upon the characteristics of the material from which the face layer is formed. However, the die cut arrays should be formed to permit separation of the identification bands from the face layer without excessive manipulation or force and without tearing either the identification bands or adjacent areas of the face layer. In certain embodiments, each die cut is a continuous die cut around the complete perimeter of all bands, cards, and/or labels. The length of each die cut and the lengths of the ties between die cuts will vary in accordance with the characteristics of the material from which the face layer is formed.

Each identification band generally includes a first end, a second opposite end, and a strap portion extending between the ends. The strap has dimensions as described herein. The strap is sufficiently large to display the required information. In certain embodiments, the strap extends substantially symmetrically between the first and second ends. However, it will be understood that the present subject matter includes straps having a variety of shapes and sizes.

In certain embodiments, the face layer also includes or defines one or more labels. Typically, the labels are selectively removable and include a region of an adhesive along their rear face as described in greater detail herein.

In certain embodiments of the present subject matter, the face layer can optionally further include an identification card formed from one or more cuts. The identification card is typically rectangular, but may also include a tab extending from one long side thereof. The face layer can define other components and/or items.

The face layer includes a top surface or face and an oppositely directed underside or rear face. The top surface of the face layer can be imprinted with patient-specific indicia at locations corresponding to the identification band(s), the labels, the optional identification card, and/or other components.

As previously noted, in many embodiments, the face layer is a composite layer and includes materials in one or more areas which are different from materials used in other areas of the face layer. For example, in certain versions, the face layer includes a first region which is formed from fibrous materials described herein. And, the face layer can further include a second region which is formed from one or more paper materials. A typical arrangement in accordance with the present subject matter is providing one or more bands in the region formed from fibrous materials, and providing one or more labels in the region formed from paper materials. However, it will be appreciated that the present subject matter includes other arrangements and/or combinations of components and layer materials.

In versions of the sheet article utilizing paper in the face layer, a variety of paper materials can be used. For many applications, a laser imprintable paper is utilized. However, the subject matter includes other paper types having different characteristics and properties such as but not limited to papers adapted for use with ink jet printers. In addition, papers adapted for use with direct thermal or thermal transfer are also contemplated.

In certain embodiments of the present subject matter, a fibrous material as described herein can be incorporated in the face layer. And, in particular embodiments, the fibrous material is utilized in one or more regions of the face layer in which the identification band(s) are provided.

In certain applications, it may be desired to apply one or more top coats to the top or face surface of the face layer. For example, in certain versions, a thermal coating layer may be deposited, formed, or otherwise provided on the face layer.

The thermal coating layer is made of a material that facilitates thermal printing, e.g., direct thermal printing, of thermally-activated images or variable information, e.g., print and barcode information, within the face layer. Thus, the thermal coating layer's material (also referred to as a direct thermally activatable material) is heat activatable. In general, the thermal coating layer comprises a low solids water, a solvent, or a solventless borne liquid that includes a stoichiometric mixture of dye, sensitizer, and developer components. Representative materials from which the thermal coating layer can be made, include but are not limited to the following: NuCoat 8957 and 8952, which are provided by NuCoat of Plymouth, Minn. Representative waterborne versions of the thermal coating layer material include about 30-50% solids. Representative embodiments of the thermal coating layer material can include a leuco dye, a sensitizer, and a developer, which are intermixed and applied as a single coating to the substrate layer material.

Because the chemistry of the thermal coating layer's material typically is vulnerable to attack by alcohols, solvents, water, and/or other contaminants, a protective barrier coat, e.g., a topcoat layer, typically is applied over the thermal coating layer to protect the thermal coating layer. The topcoat layer includes a material that is resistant to abrasion and chemical or other environmental contaminants, e.g., organic contaminants, inorganic contaminants, and biological fluids. Accordingly, the topcoat layer is a protective layer that prevents damage to, or contamination of, the thermal coating layer. The topcoat layer can include organic water, solvent, or solventless liquid(s), for example, solvent-borne acrylics or silicones that can be dried or cured to develop its properties. Also, the topcoat layer can be UV curable. Examples of topcoat layer materials include the following: varnishes and other topcoat layer material provided by Acetega of Wesel, Germany, the Flint Group of Plymouth, Mich., and Ashland Inc. of Covington, Ky., for example, Acetega 814HSMW2 and Flint UVF02052. In certain embodiments, the topcoat layer is applied with a coatweight in the range between about 5 grams per square meter and about 20 grams per square meter.

In addition to providing resistance to contaminants, the topcoat coating layer also can be print-receptive to ink(s) and other medium. If the topcoat coating layer is not receptive to ink(s) or other medium, and such receptiveness is desired, an additional coating layer can be applied over the topcoat layer, such that the additional coating layer is coupled to the topcoat layer, to impart the desired properties. The additional coating layer has a thickness which can range in value from about 0.05 mils to about 0.25 mils. Thus, the overall thickness of representative embodiments of the face layer that include the additional coating layer with the substrate layer, the thermal coating layer, and the topcoat layer can range in value from about 3.3 mils to about 6.4 mils. The additional coating layer can be made from UV, or solvent-borne acrylics or silicones, and contain materials having abrasion-resistant properties, or other additives, depending on what finished performance properties are desired. An example of the material that can be used in the additional coating layer is varnish.

Liner Layer

The sheeted articles of the present subject matter also comprise a liner or backing layer. In many embodiments, the liner layer is sized and shaped to correspond to the face layer and is adhered thereto as described herein. The liner layer is generally positioned along the face layer such that the top surface of the liner is directed toward the back surface or underside of the face layer.

In many embodiments, the liner layer is substantially rectangular and conforms to the size and shape of the face layer. The liner layer can be any flexible paper or film. In many embodiments of the present subject mater, the liner layer includes or is formed from one or more paper materials. Basically any paper with surface roughness suitable for feeding through a sheet fed printer can be used. Most roll fed printers use a super calendered (SCK) paper. In certain versions, the liner layer is a paper sheet with a thickness selected so that the sheet article can be processed efficiently through a conventional sheet-fed printer, such as a laser printer or ink jet printer. In various embodiments, the liner layer can include or be formed by a fibrous material as described herein. Currently available printers can process sheets with a thickness of 15 mils or less. A liner layer with a thickness of 2 mils to 6 mils would provide sufficient support for the sheet article while still permitting efficient processing through a conventional printing apparatus. The liner layer has a top surface, and an oppositely directed bottom or rear surface. As described in greater detail herein, a release coating is applied to one or more areas of the top surface of the liner layer that will register with the labels and one or more regions of the bands. Additional details of the release coating are provided herein.

In certain embodiments such as those which provide an identification card, the liner layer further includes an array of die cuts that will substantially register with the die cuts that define the optional identification card. Thus, the die cuts on the liner layer define an identification card support conforming to the size and shape of the identification card. For versions of the sheeted articles that do not include such card(s), the liner layer can be free of die cuts.

The back surface or underside of the face layer can be registered with, and secured to, the top surface of the liner layer to form the sheet article. The sheet article then can be processed through a printer, such as a laser printer, thermal, or inkjet printer to print patient specific indicia on at least the identification panel of each identification band, on one or more labels, and on the optional identification card. Patient specific indicia also can be printed on other portions of the top surface of the face layer.

The materials of the face layer and the liner layer of the printable sheets are selected based upon the end use requirements for the components of the sheet. In accordance with one embodiment of the present subject matter, the face layer includes or is formed from the previously described fibrous material. In accordance with other embodiments, the liner or backing layer can include the fibrous material described herein. Also and as previously noted, in forming the printable sheet assemblies described herein, a face layer composed of different materials can be used. For example, a face layer comprising one or more polymeric film materials can be used for certain regions of the sheet and different materials can be used on other regions. Similarly for example, a face layer comprising a woven material can be used in certain regions and a paper material can be used in other regions. In many embodiments of the present subject matter, the face layer is configured to be printed with indicia. The printing can be performed with a thermal printer, an inkjet printer, a laser printer, and/or by some other type of printer.

Adhesives

The various embodiment sheets typically include a layer of one or more adhesives between the face layer and the liner layer. Generally, the adhesive is a continuous layer in the region of the labels defined in the face layer. In certain embodiments and as described in greater detail herein, the adhesive layer is discontinuous in certain regions. In these embodiments, the adhesive may be pattern coated. In certain embodiments, the adhesive is a pressure sensitive adhesive.

The present subject matter includes the use of at least two adhesives in the sheet article. A permanent adhesive is used along the strap portion of the band articles in the sheet, and a releasable pressure sensitive adhesive is used in other regions of the sheet and particularly along an end (e.g., attachment end) of the band articles. In embodiments, the adhesive employed at an attachment end of the band shape is permanent pressure sensitive adhesive that has an adhesiveness that allows it to be releasable from a release material but is substantially strong enough such that it is essentially permanent when contacting the face layer during attachment of the band article. As previously noted, a pressure sensitive adhesive is also utilized in regions of the face layer that contain labels. The pressure sensitive adhesive used in association with the labels can be the same or different than the pressure sensitive adhesive used in association with the bands. Additionally, the adhesive employed in the attachment end of the band may be the same or different than the permanent adhesive employed in the strap end of the band.

In certain versions, the permanent adhesive is a hot melt rubber based permanent adhesive. Any permanent adhesive that is water resistant and bonds to the laser imprintable top coating would be a suitable candidate for use in the sheet articles. Potential suppliers of such adhesives include: HB Fuller, Henkel, Bostik, and Ashland.

The pressure sensitive adhesive has a composition that will remain stable and not flow or substantially not flow when subjected to temperatures as high as 300° F. to 400° F. These characteristics facilitate printing of the sheet assembly article in a laser printer or other high temperature printing apparatus. The adhesive also should not degrade easily when exposed to ultra-violet (UV) light. In this regard, exposure to ultra-violet light during normal use of the components of the sheet assembly should not turn the adhesive yellow or cause the adhesive to lose its tackiness. One such adhesive is described in U.S. Pat. No. 5,262,216 to Popat et al. A preferred adhesive is a hot melt adhesive which is available from Avery Dennison Corporation under the designation P32™. The pressure sensitive adhesive typically has a thickness in the range of about 0.25 mils to about 2.0 mils. Water based pressure sensitive adhesives are also suitable for many embodiments.

Release Coating

A wide variety of release coatings can be used in the sheet articles of the present subject matter. The various embodiment sheets typically include a release coating or layer of a release agent between the layer of adhesive and an adjacent layer such as the liner layer. Generally, the release agent or composition containing such is in the form of a continuous layer. In certain embodiments the release layer is discontinuous. In these embodiments, the release agent if initially in a liquid form, can be pattern coated. In certain versions, the release coating is a silicone material and more particularly, a UV cured silicone with an internally formulated release level deemed suitable for the application. Suitable suppliers include Momentive, Bluestar, Wacker, and Evonik. Other release compositions, such as fluorinated or amine based release compositions can be used. The release coating can be relatively thin, e.g., in the range of about 0.1 to 0.5 mils (2.5 microns to 13 microns).

The release agent is typically applied in a liquid form and then cured. UV curable release agents are suitable for many embodiments. UV curing release systems are generally either cationic or free radical systems. Thermally cured release agents can also be used.

Deadener

In certain versions of the present subject matter, an adhesive deadener or more particularly, a coating of a deadener material can be incorporated in certain regions of the sheet articles. One or more deadener agents can be provided along a region or face of an adhesive layer to reduce or eliminate the tackiness of the adhesive. Deadener can be applied to a previously formed region or layer of release agent that is disposed along an adhesive layer. Instead of applying the deadener agent(s) to a previously deposited release face, it is also contemplated that the deadener(s) could be incorporated within the release agent material prior to its deposition. Alternatively or in addition, the deadener(s) could also be utilized in conjunction with adhesive materials as described in greater detail herein. A variety of adhesive deadeners are known in the art such as for example, the deadeners disclosed in U.S. Pat. Nos. 5,982,284; 7,575,791; and 7,579,059.

In certain versions of the present subject matter, the release material and the deadener material are used together or in conjunction with one another. The silicone or other release agent is applied first to desired regions of the underside of the face layer, and then any area that is to exhibit reduced or no tack is coated with deadener over the silicone. For example, deadener is applied on silicone on the underside of the face layer in the strap region of a band. A permanent adhesive is coated on a corresponding region of the liner layer and then the two layers are laminated together. Upon end user removal of the band, the deadener transfers from the silicone due to adhesion between the deadener and the permanent adhesive. In particular embodiments, both the deadener and the silicone are UV cured coatings.

It is also contemplated that instead of using a combination of release agent and deadener, a temporary adhesive which exhibited relatively low levels of tack or no tack, upon separation of the layers, could potentially be used. Such a temporary bonding adhesive could be used in place of release agent, deadener, and adhesive on the portion of the strap at which a pressure sensitive adhesive is not needed on the separated band.

Identification Articles

As previously described, the various embodiment sheets may include one or more identification articles such as identification bands. The identification bands are typically attached to wrists and/or ankles of a patient in a hospital or healthcare environment. Indicia printed on the band can serve to identify the patient. Indicia printed on the band may also include information about the patient or the patient's care, therapy, or other conditions or characteristics. It will be appreciated that the present subject matter includes a wide range of uses and applications of the identification bands.

The identification band is formed from a thin flexible layer of one or more materials. The material can be a woven or nonwoven material. In certain versions, the material is the fibrous material described herein. Along a top side of the band, the band includes a material that will clearly display indicia imparted thereon by a commercially available printer, such as a laser printer, an inkjet printer, a thermal printer or the like. The material for receiving indicia can be a paper material or a non-paper material such as a polymeric or film material for example polyester, nylon polyvinyl chloride or other vinyl materials, and nonwoven or woven materials. Additionally, the fibrous material may be impregnated with a compatible synthetic material that will substantially fill voids between the fibers to define a sufficiently continuous and smooth surface for receiving and displaying printed indicia. The synthetic material impregnated into the fibrous material may be a polyester, styrene, acrylic or other compatible organic-based material. The identification band in certain embodiments is sufficiently thin and flexible to avoid irritating sensitive skin. Typical non-limiting thicknesses for the top side material of the identification band are from about 1.5 mils to about 4 mils (38 microns to 102 microns), and in certain embodiments from about 2 mils to about 3 mils (51 microns to 76 microns). Typical non-limiting thicknesses for the back side material for the identification band such as a woven material are from about 2 mils to about 5 mils (51 microns to 127 microns), and in certain embodiments about 3 mils (76 microns). Non-limiting thicknesses of an adhesive layer or regions thereof is between the top side and back side materials is from about 0.5 mils to about 1.5 mils (13 microns to 38 microns), and in certain embodiments about 1 mil (25 microns). It will be appreciated that in no way is the present subject matter limited to any of these values or dimensions.

Identification bands as described herein are particularly well suited for patients in a health care setting. Narrow width bands are especially well suited for the small wrists or ankles of infants. The band is sufficiently wide to provide the necessary strength and to prevent biting into the wrist or ankle of the patient. Additionally, the band in certain embodiments is wide enough to prevent twisting during normal use. A band of approximately 1.25 inches to about 0.25 inches (31.75 mm to 6.35 mm) wide is sufficient for these purposes. Again, the present subject matter includes a wide array of other dimensions and configurations. For example, in certain embodiments, the band has a width of from 0.25 to 2 inches (0.6 to 5.1 cm), more particularly from 0.4 to 1.5 inches (0.8 to 1.3 cm), and more particularly from 0.75 to 1.25 inches (1.9 to 3.2 cm). The band may have a length of from 4 to 12 inches 10.2 to 30.5 cm), more particularly from 5 to 11 inches (12.7 to 27.9 cm), and more particularly from 7 to 9.5 inches (17.8 to 24.1 cm).

Additional components, layers, and materials can be included in the identification bands. RFID HF or UHF components, generally referred to herein as RFID or RFID components, (such as available from Texas Instruments under the designation TAG IT or Avery Dennison's UHF products) may also be inserted during manufacturing to reside between the laminate layers, thereby securing the RFID safely, securely and permanently between or on the topside of the band. In addition, the compressible nature of a woven or non-woven fabric provides a protective cushion adjacent to the RFID to help it resist damage and can be made waterproof to further protect the identification band or RFID as well.

An important aspect of the various embodiments is the ability to print the identification band efficiently and reliably in a laser printer, thermal, an inkjet printer or other commercially available printing apparatus. Printers work best when the printed sheets are relatively thin and have uniform thickness or coplanarity across the length and width of the sheet. Sheets that are too thick may not feed well in many machines and sheets that do not exhibit coplanarity across the sheet are likely to jam or otherwise become lodged in the feed mechanisms of the printer.

The identification band of the embodiments in certain versions is part of a laminated sheet assembly that includes a face sheet and a liner or backing sheet. In certain embodiments, the face sheet is formed from the previously described fibrous material. The face sheet has a top surface on which the indicia is imprinted and a back surface that requires no indicia. In these or in other embodiments, the liner sheet may be formed from an array of materials such as paper materials with opposite top and back surfaces. In other embodiments the backing is formed from the previously described fibrous material. The top surface of the liner layer is secured at least temporarily in face-to-face engagement with the underside or rear surface of the face sheet.

In many embodiments of the identification band, at least one of the face layer and/or the liner layer is provided with at least one array of die cuts to define the shape for the identification band. The die cuts can be dimensioned to hold or further assist in retaining the identification band as part of the entire face sheet as the laminated sheet assembly is being processed through a printer. However, in certain versions of the present subject matter, die cuts that define the shape of the band are only formed in the face layer, and are not formed in the liner layer. This enables a "peel off" band as described in greater detail herein.

In a particular version of the present subject matter, a composite face layer is provided that comprises a first region formed from paper that includes a plurality of labels, and a second region formed from a fibrous material that includes one or more bands. A region of adhesive, and particularly a pressure sensitive adhesive is disposed along a rear face of the face layer in the region of the labels and on a first end of the band(s). And, sequential coatings of silicone and deadener are disposed along the rear face of the face layer in regions of the strap(s) of the band(s).

The top surface of the liner layer, i.e. the surface or face of the liner that contacts the underside of the face layer, includes a release coating in the region of the labels. And, the top surface of the liner layer also includes a region of release coating corresponding to the first end(s) of the band(s) which include region(s) of adhesive applied to the underside of the face layer. And, the top surface of the liner layer includes a region of an adhesive and particularly, a permanent adhesive along the regions corresponding to the strap(s) of the band(s). These and other aspects are described in greater detail herein.

In certain versions of the present subject matter, the identification bands exhibit particular characteristics. For example, the band can include an exposed region of a pressure sensitive adhesive at only one end of the band. In addition or alternatively, after its removal from the sheet, the band can include a rear face in the strap region that includes a deadened adhesive face.

Methods

The present subject matter also provides various methods. In one embodiment, a method of forming an article having a skin-contacting face with improved softness is provided. The method generally comprises incorporating a fibrous material as described herein in the article such that the fibrous material constitutes a skin-contacting face of the article. The methods may optionally also comprise one or more printing operations in which indicia or other markings are printed on one or more layers of the article such as on a face sheet. The printing can be performed by a thermal printing technique, an inkjet printing technique, a laser printing technique, or by some other printing technique.

As previously explained, in certain embodiments, the liner layer under the labels receives a silicone release coating. The liner layer under the band(s) receives silicone release coating only at the end portion of the band(s). A region of a pressure sensitive adhesive can be applied over the silicone release coating at the end portion of the band(s). The liner area under the strap portion of the band(s) receives permanent adhesive. The rear face or underside of the face layer in the strap portion of the band(s) corresponding with the permanent adhesive (except for the adhesive end portion of the band) receives a silicone release coating. The silicone release coating receives a deadener in this region. The face layer and the liner layer are joined together. Upon removal of the band from the sheet article, the permanent adhesive corresponding to the deadener separates the deadener from the silicone thereby simulating a non-adhesive bond or no tack. The silicone release coating remains along the strap portion. As band removal progresses to the end of the band which includes a region of a pressure sensitive adhesive, the adhesive coated over the silicone transfers to the back side of the band within the end region because there is no silicone or deadener in that region. In some embodiments the deadener is coated directly over the pressure sensitive adhesive without use of a release coating. This creates enough tack to hold the face joined with the liner thereby simulating a non-adhesive bond or no tack.

Use or incorporation of the fibrous materials described herein can provide cost savings while providing a soft skin-contacting face for an article. The fibrous materials can readily be incorporated in a sheet or web assembly and are adapted for use or passage in a wide array of printers. Many other benefits will no doubt become apparent from future application and development of this technology.

Embodiments

Figure 2:
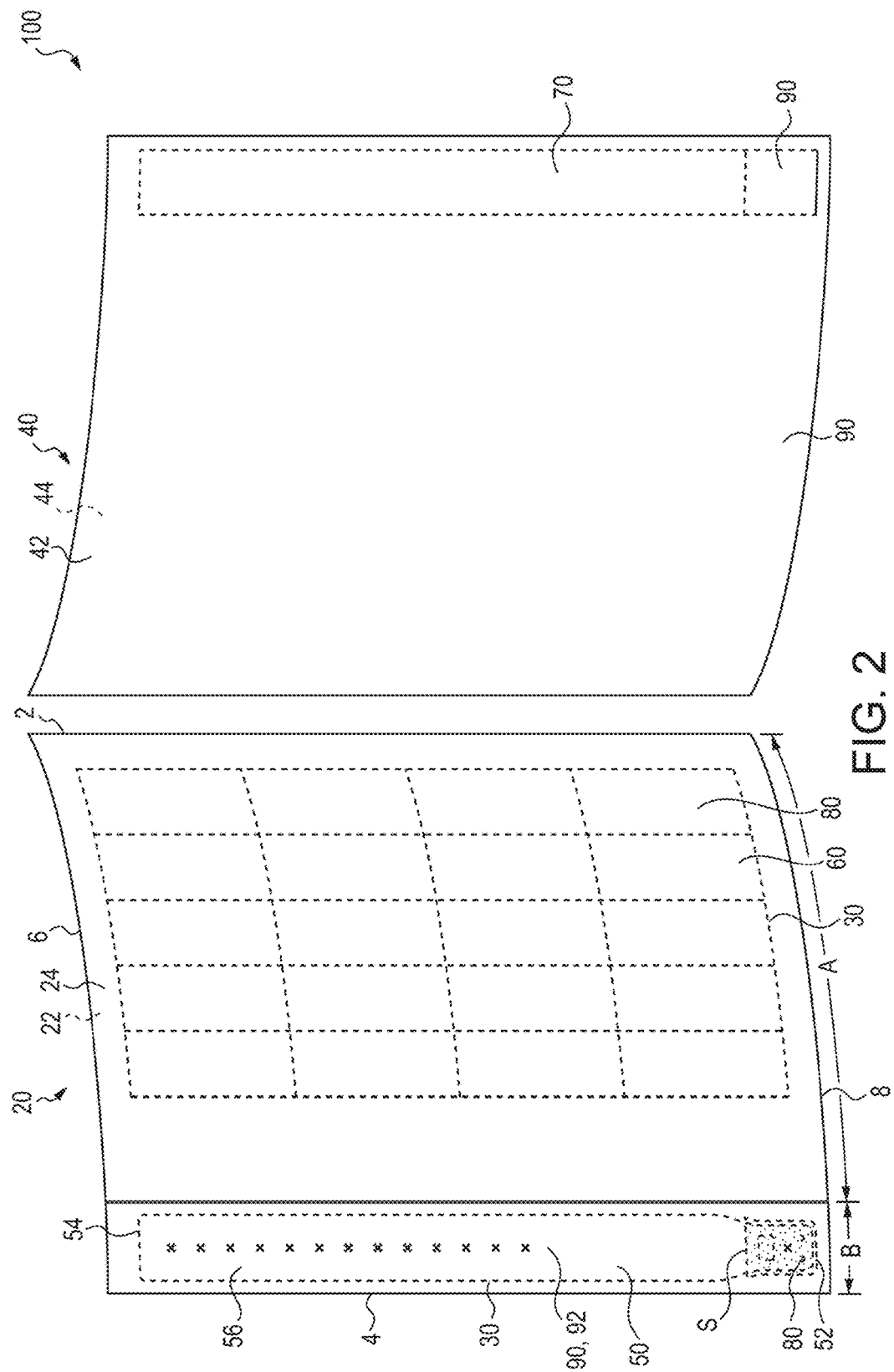
FIG. 2 is a schematic exploded view of the article depicted in FIG. 1 illustrating its components in greater detail.

FIGS. 1-6 illustrate a representative embodiment of a sheeted article 100 in accordance with the present subject matter. The article 100 comprises a face layer 20 and a liner layer 40. The layers 20 and 40 are joined to one another and include regions of adhesives, release agents, and deadeners disposed between them. Referring to FIG. 2, the face layer 20 defines a top face 22 and an oppositely directed rear face 24. The liner layer 40 defines a top face 42 and an oppositely directed bottom or rear face 44. FIG. 1 illustrates these two layers aligned and joined with one another to form the article 100.

The article 100 defines a pair of lengthwise extending edges 2 and 4, and a pair of widthwise extending edges 6 and 8. In the particular embodiment shown, edges 2 and 4 are parallel with one another and edges 6 and 8 are also parallel with one another. Furthermore, the edges 6 and 8 are perpendicular to the edges 2 and 4. The face layer 20 includes two regions such as regions A and B shown in FIG. 1. The face layer 20 includes a paper material in region A and a fibrous material in region B. The face layer 20 also defines one or more die cuts 30 that in turn, define band(s) 50, labels 60, and other optional components (not shown).

The band 50 includes a first end 52, a second opposite end 54, and a strap 56 extending between the ends 52 and 54. Referring to FIG. 2 which illustrates the underside 24 of the face layer 20, a region of a pressure sensitive adhesive 80 is disposed along and proximate an end portion of the band 50 adjacent the first end 52 of the band. A first layer of a release agent 90 and a second layer of a deadener 92 are disposed along the strap 56 and the second end 54 of the band, along the underside 24 of the face layer 20. Another region of a pressure sensitive adhesive 80 is disposed along the underside face 24 of the face layer 20 in the region of the labels 60. As will be further described in an alternate method below, the first layer of a release agent 90 and a second layer of a deadener 92 may be disposed along a region of a permanent adhesive 70. This may be achieved by implementing an alternate method of making the sheet assembly so that the band 30 does not retain the release agent 90 or deadener 92 once it is separated from the face layer 20 and the liner layer 40.

Continuing to refer to FIG. 2, the top face 42 of the liner layer 40 includes a region of release agent 90 that corresponds to the region(s) of pressure sensitive adhesive 80 associated with the labels 60 in the face layer 20. The liner layer 40 also includes a region of release agent 90 that corresponds to the region of pressure sensitive adhesive 80 associated with the first end 52 of the band 50 in the face layer 20. The liner layer 40 additionally includes a region of a permanent adhesive 70 that corresponds to the region of the release agent 90 and the deadener 92 along the strap 56 and second end 54 of the band 50. In certain versions, a gap or spacing S can be provided between the region of pressure sensitive adhesive 80 and the area of reduced or no tack resulting from the regions or layers of release agent 90 and deadener 92. A representative distance for this gap is from about 0.1 inch to about 0.5 inch (2.54 mm to 12.7 mm) and particularly about 0.125 inch (3.175 mm).

Figure 3:
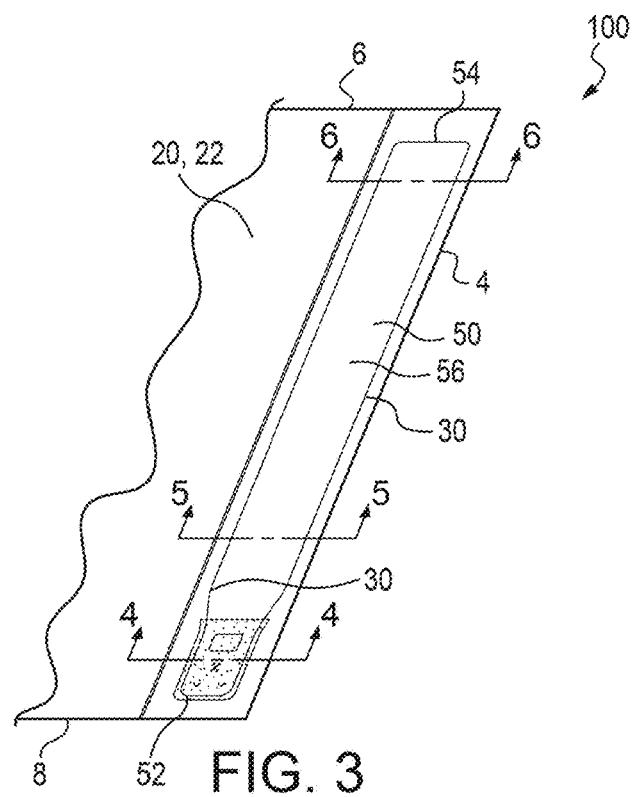
FIG. 3 is a schematic partial perspective view of a region including the removable band of the article of FIG. 1.
Figure 4:
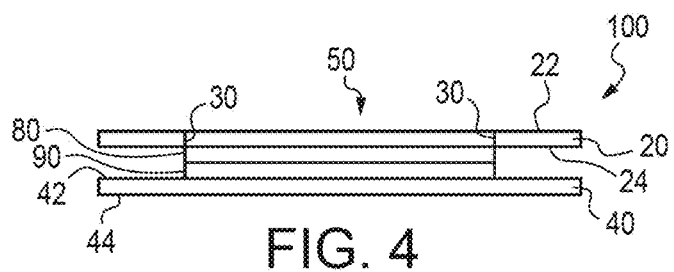
FIG. 4 is a schematic cross sectional view of the band of FIG. 3 taken across line 4-4 in FIG. 3.
Figure 5:
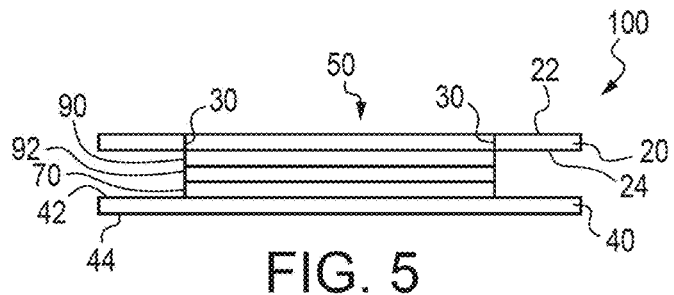
FIG. 5 is a schematic cross sectional view of the band of FIG. 3 taken across line 5-5 in FIG. 3.
Figure 6:
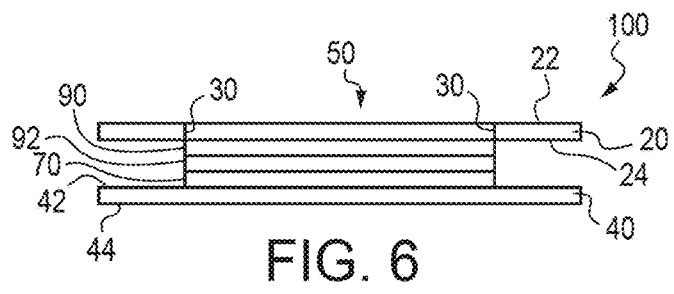
FIG. 6 is a schematic cross sectional view of the band of FIG. 3 taken across line 6-6 in FIG. 3.

FIGS. 4-6 illustrate schematic cross sectional views of the band 50 at various locations and as shown in FIG. 3. It will be appreciated that FIGS. 4-6 are schematic in nature and thus, no significance is to be attributed to the relative thicknesses of the layers. FIG. 4 is a cross sectional view of the band 50 taken along line 4-4 in FIG. 3 proximate the first end 52 of the band 50. A region of release agent 90 is disposed on the liner layer 40 and particularly, upon the top face 42 of the liner layer 40. A correspondingly shaped and sized region of a pressure sensitive adhesive 80 is disposed between the region of release agent 90 and the underside 24 of the face layer 20. FIG. 5 is a cross sectional view of the band taken along line 5-5 in FIG. 3 along the strap 56 of the band 50. A region of permanent adhesive 70 is disposed on the liner layer 40 and particularly, upon the top face 42 of the liner layer 40. A correspondingly shaped and sized region of release agent 90 is disposed along the underside 24 of the face layer 20. And, a correspondingly shaped and sized region of deadener 92 is disposed between the region of release agent 90 and the region of permanent adhesive 70. FIG. 6 is a cross sectional view of the band 50 taken along line 6-6 in FIG. 3 proximate the second end 54 of the band 50. The materials and arrangement of layers depicted in FIG. 6 is the same as that shown in FIG. 5. This is because in the particular band embodiment 50, the regions at which lines 5-5 and 6-6 are taken, utilize the same configuration. However, it will be appreciated that the present subject matter includes bands having structures or utilizing different materials and/or layers at different regions.

Figure 7:
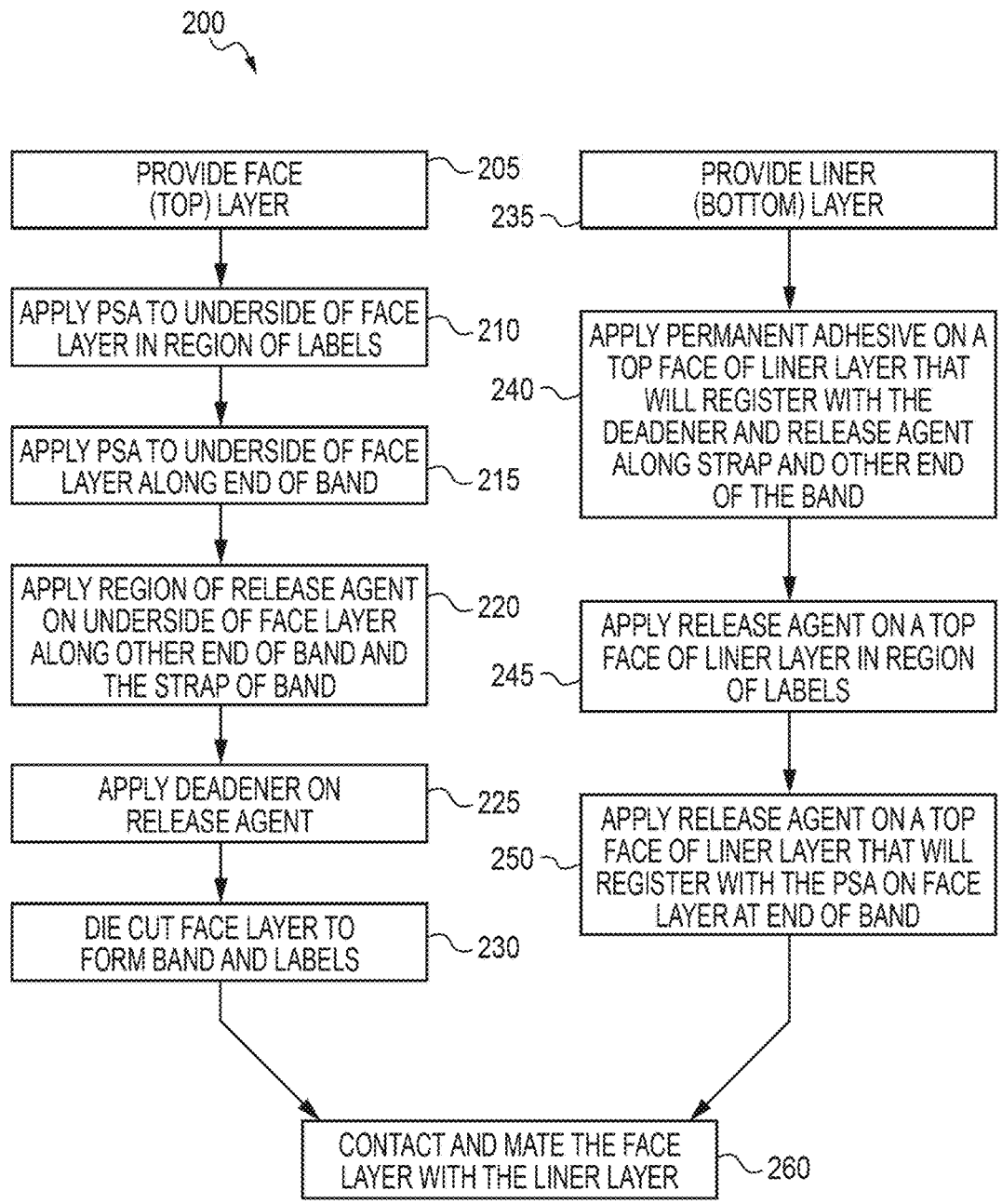
FIG. 7 is a process schematic flow chart illustrating a method of forming a sheeted article in accordance with the present subject matter.

FIG. 7 is a flow chart illustrating a method 200 for forming a sheet article in accordance with the present subject matter. The method 200 comprises a series of operations involving a face layer such as the previously described face layer 20, and a series of operations involving a liner layer such as the previously described liner layer 40. The method 200 generally comprises providing a face layer, as denoted by operation 205. In operation 210, a coating or layer of a pressure sensitive adhesive is applied to the underside of the face layer in the region of any labels, such as labels 60 depicted in FIG. 2. In operation 215, a coating or layer of a pressure sensitive adhesive is applied to the underside of the face layer along an end of the band, such as region 80 depicted in FIG. 2. In operation 220 a coating or layer of a release agent such as a silicone release agent is applied on the underside of the face layer along the other end of the band and along the strap region of the band. This is shown as region 90 in FIG. 2. In operation 225, one or more deadener agent(s) is applied on the release agent previously applied in operation 220. Deadener 92 is shown along the underside of the face sheet and on the release agent 90, in FIG. 2. In operation 230, the face layer is appropriately die cut or subjected to other operation(s) to thereby define the band and labels.

The method 200 also comprises an operation of providing the liner layer, such as in operation 235. In operation 240, a permanent adhesive is applied on the top face of the liner layer that will register with the deadener and release agent along the strap and an end of the band. FIG. 2 illustrates a region 70 of permanent adhesive applied in such manner. In operation 245, a release agent is applied on the top face of the liner layer in the region of the labels. This is shown in FIG. 2 in which release agent 90 is disposed on the liner 40 in a region corresponding to the labels 60. In operation 250, a release agent is applied on the top face of the liner layer that will register with the pressure sensitive adhesive on the face layer at an end of the band. This is shown in FIG. 2 in which a region 90 of release agent is disposed on the liner 40 at a location that will register with the pressure sensitive adhesive 80 on the face layer 20 at the end 52 of the band. And, the method 200 comprises an operation 260 of contacting and mating the face layer and the liner layer with one another to thereby form a sheet article.

It will be understood that the present subject matter includes variations of the method 200. For example, die cutting operations shown as operation 230 in FIG. 7 could be performed prior to or after one or more other operations illustrated. Furthermore, if the sheet article does not include labels, then operations such as operation 210, are not necessary.

Figure 8:
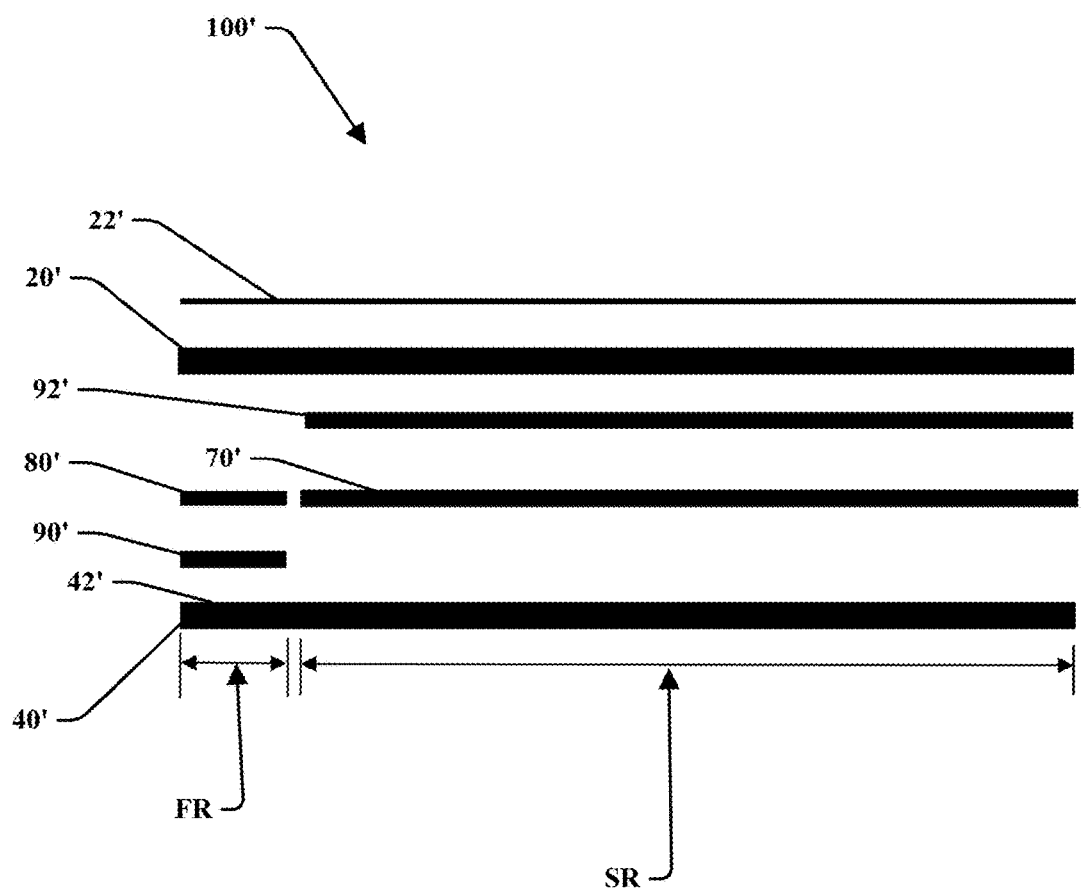
FIG. 8 is a schematic cross sectional view of embodiments of the sheet assembly.

FIG. 8 illustrates an alternate embodiment of the liner layer and face layer of the present disclosure in which like figures will be described with similar reference numbers denoted with a prime (') reference. FIG. 8 is a cross sectional view that is schematic in nature and thus, no significance is to be attributed to the relative thicknesses or sizes of the layers. In this embodiment, a portion of release agent 90' may be disposed on the liner layer 40' at a first region FR and particularly, upon the top face 42' of the liner layer 40'. A correspondingly shaped and sized portion of a pressure sensitive adhesive 80' may be disposed on the release agent 90' along the first region FR upon the top face 42' of the liner layer 40'.

The first region FR indicates an area that may be generally aligned with the first end 52 of the band 50 and a second region SR may be separate from the first region FR and may indicate an area that may be generally aligned with a perimeter of the strap 56 of the band 50. A portion of adhesive 70' may be disposed on the liner layer 40' and particularly, upon the top face 42' of the liner layer 40' along the second region SR. A portion of deadener 92' may be correspondingly shaped and sized relative to the shape and size of the strap 56 of the band 50 may be disposed along at least a portion of the second region SR on the top face 42' of the liner layer 40'. This embodiment allows the band to be removed from the face layer 20' and the liner layer 40' such that the adhesive 80' may be transferred to the underside of the face layer 20' without having release agent 90' or deadener 92' remaining on the band. However, it will be appreciated that the present subject matter includes bands having structures or utilizing different materials and/or layers at different regions. An alternative embodiment allows the band to be removed from the face layer 20' and the liner layer 40' such that the adhesive 80' may remain adhered to the top side of the liner layer 40 and covered at least partially with deadener 92 without having any release coating on face layer 20'. However, it will be appreciated that the present subject matter includes bands having structures or utilizing different materials and/or layers at different regions.

In another embodiment, a dry peel coating may be disposed along the underside of the face layer 20' along the second region SR there by negating the need for a deadener 92' along the second region SR of the liner layer 40'. The dry peel coating may be a hot melt or a water based material that allows the band to be removed from the face layer and the liner layer without adhesive transferring to the second region SR of the band of the face layer.

Figure 9:
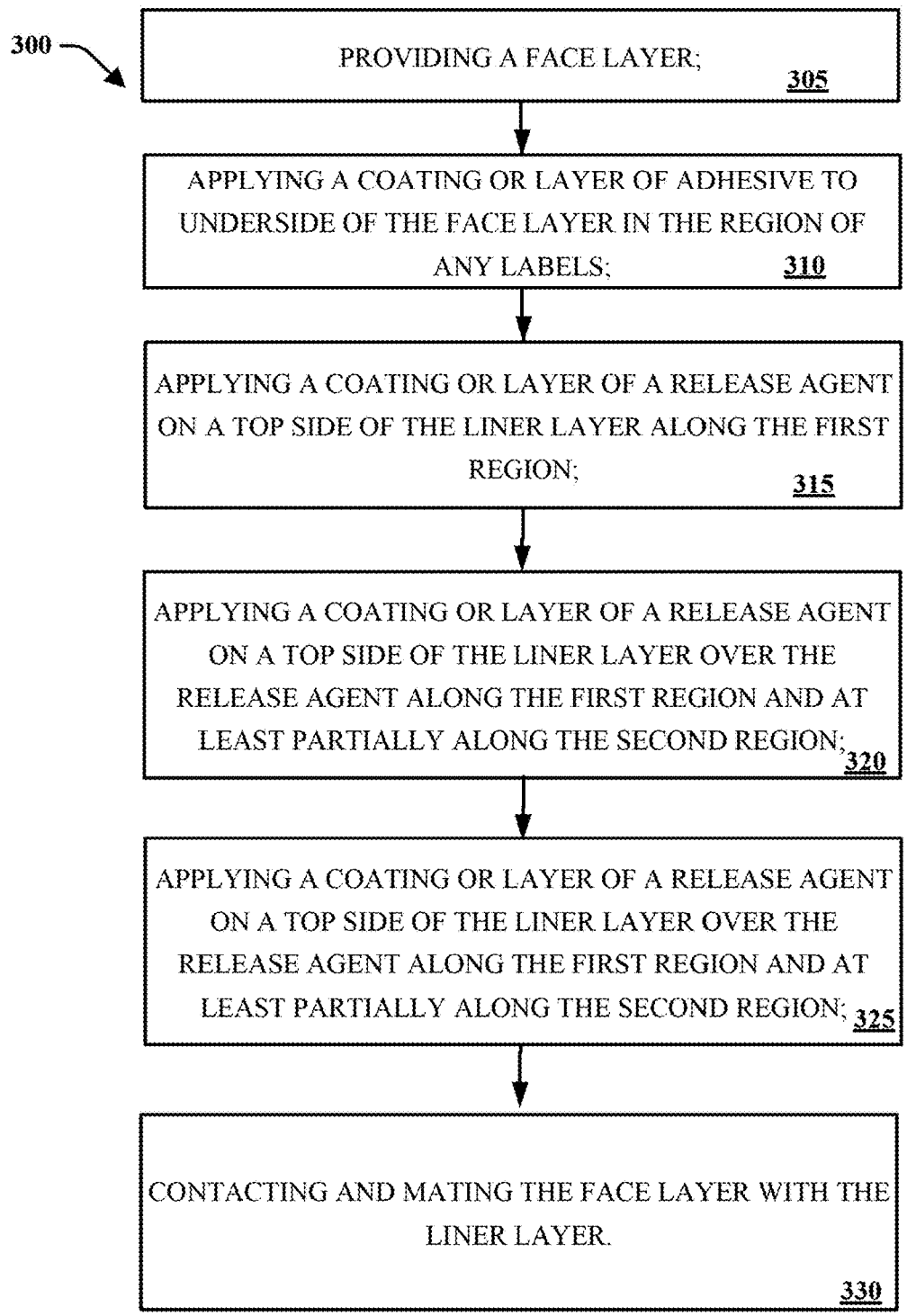
FIG. 9 is a schematic flow chart illustrated a method of forming a sheet article in sheeted article in accordance with the present subject matter.

In a further aspect, the present subject matter provides a method for making the sheet article of FIG. 8. FIG. 9 is a flow chart illustrating a method 300 for forming a sheet article in accordance with the present subject matter. The method 300 comprises a series of operations involving a face layer such as the previously described face layer 20', and a series of operations involving a liner layer such as the previously described liner layer 40'. The method 300 generally comprises providing a face layer, as denoted by operation 305. In operation 310, a coating or layer of an adhesive is applied to the underside of the face layer in the region of any labels, such as labels 60 depicted in FIG. 2. In operation 315, a coating or layer of a release agent 90' such as a silicone release agent is applied on the top side of the liner layer along the first region FR that is to correspond to the first end of the band and along the strap region of the band. This is shown as region 90 in FIG. 2. In operation 320, a coating or layer of a pressure sensitive adhesive 80' may be applied over the release agent 90' and a coating or layer of an adhesive 70' may be applied to the top side 42' of the liner layer 40' along the second region SR that is comparable to region 70 depicted in FIG. 2. In operation 325, one or more deadener agent(s) 92' may be applied on the adhesive 70' previously applied in operation 320. Deadener 92' is shown along the top side of the liner layer 40' and on the adhesive 70' in FIG. 8. In operation 330, the face layer 20' may contact and mate with the liner layer.

Figure 10:
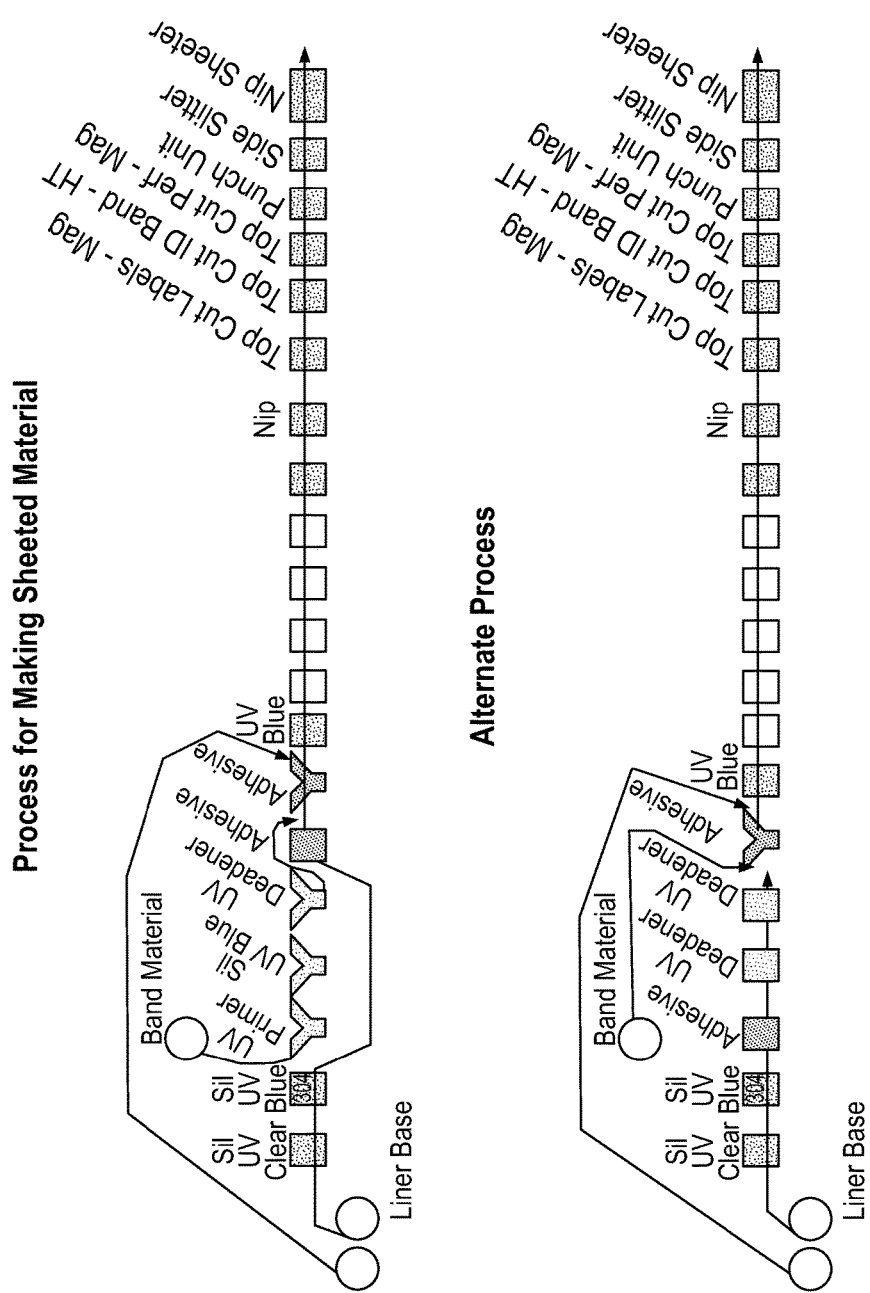
FIG. 10 is a schematic diagram illustrating embodiments of a method of forming a sheet article in accordance with the present subject matter.

The method 300 may also include operational steps of die cutting the band from the face layer and applying a layer of imprintable coating on the face layer. The band may be separable from the face layer by one or more die-cuts defining the band perimeter. FIG. 10 is provided to illustrate various steps of the method of making the sheeted article. All patents, applications, standards, and articles noted herein are hereby incorporated by reference in their entirety.

As described hereinabove, the present subject matter overcomes many problems associated with previous strategies, systems and/or articles. However, it will be appreciated that various changes in the details, materials and arrangements of components, which have been herein described and illustrated in order to explain the nature of the present subject matter, may be made by those skilled in the art without departing from the principle and scope of the claimed subject matter, as expressed in the appended claims.

What is claimed is:

1. A sheeted article providing at least one identification band comprising:
   a face layer having an upper surface and a lower surface and defining at least one identification band, the at least one identification band having a first region proximate a first end, and a second region defined by a second end and a strap extending between the first and second end;
   a dry peel release coating disposed on the lower surface of the face layer within the second region;
   a liner layer;
   a release material disposed on a first region of the liner layer proximate and in contact with the region of pressure sensitive adhesive; and
   a region of pressure sensitive adhesive overlying the release material;
   a permanent adhesive disposed on a second region of the liner extending along at least a majority of the strap and the second end of the band defined by the face layer, the permanent adhesive being chosen from a hot melt adhesive.

2. A sheeted article providing at least one identification band comprising:
   a face layer having an upper surface and a lower surface and defining at least one identification band, the at least one identification band having a first region proximate a first end, and a second region defined by a second end and a strap extending between the first and second end;
   a liner layer;
   a release material disposed on the liner layer in an area corresponding to the first region of the band;
   a first adhesive overlying the release material;
   a second adhesive disposed on the liner extending along at least a majority in an area corresponding to the second region of the band, the second adhesive being chosen from a hot melt adhesive; and
   a deadener disposed on the second adhesive; wherein upon removal of the identification band from the sheeted article, the first region of the identification band comprises the region of pressure sensitive.

3. The sheeted article of claim 2, wherein upon removal of the identification band from the sheet, the second region is free of deadener.

4. The sheeted article of claim 2, wherein the first adhesive is a pressure sensitive adhesive.

5. The sheeted article of claim 2, wherein the second adhesive is a permanent adhesive.

6. The sheeted article of claim 2, wherein the release material first adhesive is substantially coextensive with the release material.

7. The sheeted article of claim 2, wherein the deadener is substantially coextensive with the second adhesive.

8. The sheeted article of claim 2, wherein the face layer is formed from paper, a woven material, a non-woven material, a spun material, a polymer film, or a combination of two or more thereof.

9. The sheeted article of claim 2, wherein the face layer comprises a material chosen from a polyethylene, a polypropylene, a polyethylene terephthalate, a polyvinyl chloride, or a combination of two or more thereof.

10. The sheeted article of claim 2, wherein the face layer comprises a non-woven polyester material laminated to a polyester film.

11. The sheeted article of claim 10, wherein the non-woven polyester film forms the lower surface of the face layer.

12. The sheeted article of claim 10, wherein the non-woven polyester material has a thickness of from about 1 mil to about 4 mils, and the polyester film has a thickness of from about 0.5 mils to about 4 mils.

13. The sheeted article of claim 2, wherein the first adhesive comprises a first permanent adhesive and the second adhesive comprises a second permanent adhesive.

14. The sheeted article of claim 13, wherein the first permanent adhesive is different than the second permanent adhesive.

15. The sheeted article of claim 2, wherein (a) the face layer comprises (i) a label region with at least one label defined therein, and (ii) a third adhesive on the lower surface of the face layer along the label; and (b) the liner layer comprises a release material in an area corresponding to the label region.

16. The sheeted article of claim 2, wherein upon removal of the wristband from article, the second region of the band is free of deadener, and the deadener overlies the second adhesive disposed on the liner.

17. A method of forming a sheeted article having a removable identification band, the method comprising:
providing a face layer having an upper surface and a lower surface;
die cutting a band in the face layer, the band having a first region proximate a first end, and a second region defined by a second end and a strap extending between the first and second end;
providing a liner layer comprising an upper surface and a lower surface;
applying a release coating on the upper surface of the linear in a region corresponding to the first region of the band;
applying a first adhesive over the release agent;
applying a second adhesive on the upper surface of the liner in a region corresponding to the second region of the band, the second adhesive being chosen from a hot melt adhesive;
applying a deadener over the second adhesive; and
mating the face layer with the liner layer.

18. The method of claim 17, wherein the first adhesive is a pressure sensitive adhesive.

19. The method of claim 17, wherein the second adhesive is a permanent adhesive.

20. The method of claim 17, wherein mating is performed by aligning the face layer with the liner layer and contacting the lower surface of the face layer with the upper surface of the liner layer.

21. The method of claim 17 further comprising die cutting at least one label in a label region of the face layer.

22. The method of claim 21 further comprising applying a pressure sensitive adhesive along the lower surface of the label region of the face layer.

23. The method of claim 21 further comprising applying a release agent to the upper surface of the liner layer in a region that will register with the label region of the face layer.

24. The method of claim 17, wherein the face layer is formed from paper, a woven material, a non-woven material, a spun material, a polymer film, or a combination of two or more thereof.

25. The method of claim 17, wherein the face layer comprises a material chosen from a polyethylene, a polypropylene, a polyethylene terephthalate, a polyvinyl chloride, or a combination of two or more thereof.

* * * * *